US006852894B2

(12) United States Patent
Ching (10) Patent No.: US 6,852,894 B2
(45) Date of Patent: Feb. 8, 2005

(54) TRIBENZOYL COMPOUNDS (75) Inventor: Ta Yen Ching, Houston, TX (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 0 days.

(21) Appl. No.: 10/289,650

(22) Filed: Nov. 7, 2002

(65) Prior Publication Data

US 2003/0062505 A1 Apr. 3, 2003

Related U.S. Application Data

(62) Division of application No. 09/630,618, filed on Aug. 2, 2000, now abandoned, which is a continuation of application No. 08/857,325, filed on May 16, 1997, now Pat. No. 6,139,770.

(51) Int. Cl.[7] ..................... C07C 49/215; C07C 49/227; C07C 49/255

(52) U.S. Cl. ....................... 568/326; 568/327; 568/332; 568/337

(58) Field of Search ................................ 568/326, 332, 568/322, 323, 331, 327, 337; 252/600; 522/36, 46

(56) References Cited

U.S. PATENT DOCUMENTS

| | | | | |
|---|---|---|---|---|
| 2,069,683 | A | * | 2/1937 | Scholl et al. |
| 3,497,571 | A | | 2/1970 | Tellier et al. |
| 3,663,712 | A | | 5/1972 | von Schmeling ........... 424/330 |
| 3,954,868 | A | | 5/1976 | von Schmeling |
| 3,979,459 | A | | 9/1976 | Rose |
| 4,147,728 | A | * | 4/1979 | Rabilloud et al. |
| 4,415,710 | A | | 11/1983 | Barnabeo et al. ........... 525/370 |
| 4,524,201 | A | | 6/1985 | Barnabeo et al. ........... 528/395 |
| 4,672,079 | A | | 6/1987 | Li Bassi et al. ............... 522/35 |
| 5,095,099 | A | * | 3/1992 | Parkinson et al. ...... 568/326 X |
| 5,116,916 | A | | 5/1992 | Young ......................... 525/350 |

FOREIGN PATENT DOCUMENTS

| | | | |
|---|---|---|---|
| EP | 0 822 221 A | 2/1998 | |
| JP | SHO 60-8303 | 1/1985 | ............. C08F/2/50 |
| JP | SHO64-42452 | 2/1989 | ........... C07C/49/84 |
| WO | 96/29362 | 9/1996 | |
| WO | 96/33156 | 10/1996 | |
| WO | WO 97/05100 | 2/1997 | ......... C07C/233/49 |
| WO | WO 97/05101 | 2/1997 | ......... C07C/233/49 |
| WO | WO 97/07161 | 2/1997 | ......... C08K/5/3492 |
| WO | WO99/48963 | 9/1999 | |

OTHER PUBLICATIONS

N. Nakamura et al.: "Synthesis and Characterization of a Branched—Chain Hexa–Carbene in a Tridecet Ground State. An Approach to Superparamagnetic Polycarbenes", J. Am. Chem. Soc. 1992, 114, 1484–1485.*

K. Matsuda et al.: "Exploratory and Mechanistic Studies of the Trimerization Reaction of Benzoyl Acetylenes in the Presence of a Secondary Amine", Chemistry Letters, pp. 1765–1768, 1994.*

C. David et al., "Photolysis of Polyvinylbenzophenone", Polymer, 10 (1969), month is unknown, pp. 21–27.

J. Barton et al., "Polymerization of Vinyl Monomers Photoinitiated by Benzoylated Polystyrene", Makromol. Chem. 179 (1978), month is unknown, pp. 2937–2943.

Primary Examiner—Daniel S. Metzmaier
(74) Attorney, Agent, or Firm—Williams, Morgan & Amerson, P.C.

(57) ABSTRACT

An oxygen scavenging composition or system is provided comprising an oxygen scavenging material, a photoinitiator, and at least one catalyst effective in catalyzing an oxygen scavenging reaction, wherein the photoinitiator comprises a benzophenone derivative containing at least two benzophenone moieties. A film, a multi-phase composition, a multi-layer composition, a multi-layer film, an article comprising the oxygen scavenging composition, a method for preparing the oxygen scavenging composition, and a method for scavenging oxygen are also provided. Non-extractable benzophenone derivative photoinitiators and methods for preparing same are also provided.

2 Claims, 3 Drawing Sheets

| | | | |
|---|---|---|---|
| 5,211,875 A | 5/1993 | Speer et al. | 252/188.28 |
| 5,346,644 A | 9/1994 | Speer et al. | 252/188.28 |
| 5,425,896 A | 6/1995 | Speer et al. | 252/188.28 |
| 5,466,756 A | 11/1995 | Roach et al. | 525/330.6 |
| 5,498,364 A | 3/1996 | Speer et al. | 252/188.28 |
| 5,627,239 A | 5/1997 | Ching et al. | 525/330.6 |
| 5,641,825 A | 6/1997 | Bacskai et al. | 524/398 |
| 5,656,692 A | 8/1997 | Hayes | 525/63 |
| 5,660,761 A | 8/1997 | Katsumoto et al. | 252/188.28 |
| 5,700,554 A | 12/1997 | Speer et al. | 428/220 |
| 5,736,616 A | 4/1998 | Ching et al. | 525/330.3 |
| 5,776,361 A | 7/1998 | Katsumoto et al. | 252/188.28 |
| 5,837,158 A | 11/1998 | Shepodd et al. | 252/181.6 |
| 5,859,145 A | 1/1999 | Ching et al. | 525/330.6 |
| 6,057,013 A | 5/2000 | Ching et al. | 428/35.7 |
| 6,063,307 A | 5/2000 | Shepodd et al. | 252/181.6 |
| 6,139,770 A * | 10/2000 | Katsumoto et al. | 252/188.28 |

Cryovac U.S. application No. 08/857,226, filed May 16, 1997, entitled "Low Migratory Photoinitiators for Oxygen Scavenging Compositions".

Ching et al., "Tasteless Oxygen Scavenging Polymers: A New Platform Technology for Food Packaging Based On Controlled Oxidation," *Oxygen Absorber . . . 2001 and Beyond,* OSP Conference, pp. 1–8 (Chicago, Jun. 19–20, 2000).

Ching et al., "Tasteless Oxygen Scavenging Polymers: A New Platform Technology for Food Packaging Based On Controlled Oxidation," *Oxygen Absorber . . . 2001 and Beyond,* OSP Conference Slides (Chicago, Jun. 19–20, 2000).

* cited by examiner

TRIBENZOYL COMPOUNDS

This is division of application Ser. No. 09/630,618, filed Aug. 2, 2000, now abandoned, which is a continuation of prior application Ser. No. 08/857,325, filed May 16, 1997, now U.S. Pat. No. 6,139,770.

FIELD OF THE INVENTION

The present invention relates to photoinitiators, methods for preparing and using same, oxygen scavenging compositions, articles made from same and methods of scavenging oxygen.

BACKGROUND OF THE INVENTION

The term "oxygen scavenging" means to absorb, deplete, or react with oxygen from a given environment.

Oxygen scavenging materials have been developed partly in response to the food industry's goal of having longer shelf-life for packaged food. One method which is currently being employed involves the use of "active packaging" where the package is modified in some way so as to control the exposure of the product to oxygen. Such "active packaging" can include sachets containing iron-based compositions such as AGELESS™ which scavenges oxygen within the package through an oxidation reaction. However, such an arrangement is not advantageous for a variety of reasons including the accidental ingestion of the sachets or the oxygen scavenging material present therein.

Other techniques involve incorporating an oxygen scavenger into the package structure itself. In such an arrangement, oxygen scavenging materials constitute at least a portion of the package, and these materials remove oxygen from the enclosed package volume which surrounds the product or which may leak into the package, thereby, in the case of food products, inhibiting spoilage and prolonging freshness.

Oxygen scavenging materials include low molecular-weight oligomers that are typically incorporated into polymers or can be oxidizable organic polymers. Such oxygen scavenging materials are typically employed with a suitable catalyst, e.g., an organic or inorganic salt of a transition metal catalyst.

The onset of useful oxygen scavenging activity may not occur for as long as 30 days. In order to shorten the induction period and to initiate oxygen scavenging, photoinitiators can be employed in conjunction with actinic radiation. Many of these photoinitiators and resulting by-products are extractable and can leach into the headspace surrounding the packaged product or even enter the product itself. Such leaching can produce foul odors or unpleasant taste or can be otherwise undesirable.

SUMMARY OF THE INVENTION

It is an object of the present invention to provide a composition effective for oxygen scavenging under typical storage conditions.

It is another object of the present invention to provide a composition which is effective for oxygen scavenging at low temperatures.

It is another object of the present invention to provide an oxygen scavenging composition which produces reduced levels of extractable compounds.

It is another object of the present invention to provide an oxygen scavenging composition which has a short initiation period upon activation.

It is another object of the present invention to provide an oxygen scavenging composition which exhibits improved shelf life prior to activation.

It is another object of the present invention to provide a film or a multi-layer film capable of scavenging oxygen.

It is another object of the present invention to provide an article, package or container suitable for oxygen scavenging.

It is another object of the present invention to provide a method for preparing an oxygen scavenging composition.

It is another object of the present invention to provide a method for scavenging oxygen.

It is another object of the present invention to provide novel photoinitiators which are effective initiators for oxygen scavenging.

It is another object of the present invention to provide novel photoinitiators which are essentially non-leachable.

It is another object of the present invention to provide methods for preparing novel photoinitiators.

According to the present invention, an oxygen scavenging composition or system is provided comprising an oxygen scavenging material, a photoinitiator, and at least one catalyst effective in catalyzing the oxygen scavenging reaction. The photoinitiator comprises a benzophenone derivative containing at least two benzophenone moieties. A film, a multi-phase composition, a multi-layer composition, a multi-layer film, an article comprising the oxygen scavenging composition, as well as a method for preparing the oxygen scavenging compositions, and a method for scavenging oxygen are also provided.

According to other aspects of the present invention, non-extractable photoinitiators and methods for preparing same are provided.

DETAILED DESCRIPTION OF THE INVENTION

It has been found that benzophenone derivatives containing at least two benzophenone moieties act as effective photoinitiators to initiate oxygen scavenging activity in oxygen scavenging compositions and to provide a composition having a very low degree of extraction of the photoinitiators which may contaminate a packaged product. By benzophenone moiety is meant a substituted or unsubstituted benzophenone group. Suitable substituents are any substituent which does not interfere with the objects of the invention and include alkyl, aryl, alkoxy, phenoxy, and alicylic groups containing from 1 to 24 carbon atoms or halides.

These derivatives are substantially non-extractable by most organic solvents at room temperature. By substantially non-extractable is meant that less than about 500 ppb photoinitiator are extracted through a 0.5 mil polyethylene film in ten days at room temperature from an oxygen scavenging composition containing 1000 ppm by weight photoinitiator when exposed to 10 g fatty food simulant per square inch of 1 mil film, preferably 250 ppb photoinitiator or less are extracted, more preferably 100 ppb photoinitiator or less are extracted, and most preferably 50 ppb photoinitiator or less are extracted.

Such benzophenone derivatives include dimers, trimers, tetramers, and oligomers of benzophenone-type photoinitiators derived from benzophenone and substituted benzophenones, as fully described herein below.

The substantially non-extractable photoinitiators are represented by the following formula:

$X_m(Y)_n$

Wherein each X is a bridging group selected from the group consisting of sulfur; oxygen; carbonyl; —SiR$_2$—, wherein each R is individually selected and is an alkyl group containing from 1 to 12 carbon atoms, an aryl group containing 6 to 12 carbon atoms, or an alkoxy group containing from 1 to 12 carbon atoms; —NR'—, wherein R' is an alkyl group containing 1 to 12 carbon atoms, aryl group containing 6 to 12 carbon atoms, or hydrogen; and an organic group containing from 1 to 50 carbon atoms, preferably from 1 to 40 carbon atoms. X can be a divalent group or can be a polyvalent group with 3 or more benzophenone moieties attached. Wherein m is 0 to 11.

The organic bridging group, when present, can be linear, branched, cyclic including fused or separate cyclic groups or an arylene group which can be fused or non-fused polyaryl groups. The organic bridging group can contain one or more heteroatoms such as oxygen, nitrogen, phosphorous, silicon or sulfur or combinations thereof. Oxygen can be present as an ether, ketone, ester, or alcohol.

Wherein each Y is a substituted or unsubstituted benzophenone group. Wherein each substituent, R", when present, is individually selected from any substituent which does not substantially interfere with the objects of the invention and include alkyl, aryl, alkoxy, phenoxy, or alicyclic groups containing from 1 to 24 carbon atoms, or halides. Each benzophenone moiety can have up to 9 substituents. Wherein n is 2–12.

Preferably, the combined molecular weight of the X and R" groups is at least about 30 g/mole. Appropriate choice of substituents can render the photoinitiator more compatible with the oxygen scavenging composition. Such substituents include alkyl and alkoxy for example.

Preferably, the oxygen scavenging composition consumes half of the available oxygen in a container containing 1 percent oxygen in less than 4 days at 25° C. More preferably, the oxygen scavenging composition consumes half of the available oxygen in a container containing 1 percent oxygen in less than 4 days at 4° C.

The photoinitiators include multiplets of ultraviolet (UV) initiators linked by cross conjugation so as to retain the UV absorption characteristics with enhanced UV absorptivity, i.e., higher extinction coefficient. The linkages within the dimers, trimers, tetramers, and oligomers can be flexible or rigid. The rigid type are preferred for lower extractability. However, a certain degree of flexibility is required to facilitate the melt blending to allow a molecular level distribution in the polymer films.

Typically, these compounds have a strong UV absorption at about 200–400 nm. Generally, the molecular weight will be greater than about 360 g/mole, preferably in the range of from about 360 g/mole to about 5000 g/mole, more preferably in the range of from 390 g/mole to 4000 g/mole.

The photoinitiators are substantially non-extractable by most organic solvents when incorporated into oxygen scavenging compositions. They provide efficient light absorption to trigger a photochemical induced oxidation. The photoinitiators are stable and do not fragment into extractable by-products. The photoinitiators are also large enough or rigid enough to be immobile and therefore cannot be leached into the packaged food or product. The photoinitiators do not sublime under normal processing and handling conditions. This assures an extended shelf life for the preactivated composition and a safe packaging material according to U.S. Food and Drug Administration standards.

Examples of non-extractable photoinitiators include dibenzoyl biphenyl, substituted dibenzoyl biphenyl, benzoylated terphenyl, substituted benzoylated terphenyl, tribenzoyl triphenylbenzene, substituted tribenzoyl triphenylbenzene, benzoylated styrene oligomer, and substituted benzoylated styrene oligomer. Benzoylated styrene oligomer is a mixture of compounds containing from 2 to 12 repeating styrenic groups comprising dibenzoylated 1,1-diphenyl ethane, di-benzoylated 1,3 diphenyl propane, di-benzoylated 1-phenyl naphthalene, dibenzoylated styrene dimer, dibenzoylated styrene trimer and tribenzoylated styrene trimer.

Suitable substituents for the above compounds include any substituent which does not interfere substantially with the objects of the invention and include alkyl, aryl, alkoxy, phenoxy, and alicyclic groups containing from 1 to 24 carbon atoms or halides.

Typical examples of suitable alkyl groups include methyl, ethyl, propyl, isopropyl, butyl, t-butyl, pentyl, dodecyl, hexadecyl, octadecyl and the like. Specific examples of alkoxy groups include methoxy, ethoxy, propoxy, butoxy, dodecyloxy and the like. Examples of alicyclic groups include cyclopentyl, cyclohexyl, cycloheptyl and the like. The hydrocarbon substituents can be saturated or can contain ethylenic unsaturation.

Examples of specific photoinitiators include 4,4'-bis(4,4'-dimethyidibenzoyl) biphenyl; 4,4'-bis(4,4'-diethyidibenzoyl) biphenyl; 4,4'-bis(2,2'-dimethyldibenzoyl) biphenyl; 4,4'-bis(2,2'-dimethoxydibenzoyl) biphenyl; 4,4'-bis(4-dodecyidibenzoyl) biphenyl; 4,4'-bis(2,2'-diacetyldibenzoyl) biphenyl; 4,4-bis(4,4'-dimethyldibenzoyl) diphenyl ether; 4,4'-bis(4,4'-diethyidibenzoyl) diphenyl ether; 4,4'-bis(2,2-dimethyldibenzoyl) diphenyl ether; 4,4'-bis(2,2'-dimethoxydibenzoyl) diphenyl ether; 4,4'-bis(4-dodecyldibenzoyl) diphenyl ether; 4,4'-bis(2,2'-diacetyldibenzoyl)diphenyl ether; 4,4'-bis(4,4'-dimethyldibenzoyl)diphenyl sulfide; 4,4'-bis-diethyldibenzoyl)diphenyl sulfide; 4,4'-bis(2,2'-dimethyldibenzoyl)diphenyl sulfide; 4,4'-bis(2,2'-dimethoxydibenzoyl) diphenyl sulfide; 4,4'-bis(4-dodecyldibenzoyl) diphenyl sulfide; 4,4'-bis(2,2'-diacetyldibenzoyl) diphenyl sulfide; 4,4'-bis(4,4'-dimethyldibenzoyl) diphenyl amine; 4,4'-bis(4,4'-diethyldibenzoyl) diphenyl amine; 4,4-bis(2,2'-dimethyidibenzoyl) diphenyl amine; 4,4'-bis(2,2'-dimethoxydibenzoyl) diphenyl amine; 4,4'-bis(4-dodecyldibenzoyl) diphenyl amine: 4,4'-bis(2,2'-diacetyldibenzoyl) diphenyl amine; 4,4'-bis(4,4'-dimethyidibenzoyl) diphenyl dimethyl silane; 4,4'-bis(4,4'-diethyidibenzoyl) diphenyl dimethyl silane; 4,4'-bis(2,2'-dimethyidibenzoyl) diphenyl dimethylsilane; 4,4'-bis(2,2'-dimethoxydibenzoyl) diphenyl dimethyl silane; 4,4'-bis(4-dodecyldibenzoyl) diphenyl dimethyl silane; 4,4'-bis(2,2'-diacetyldibenzoyl) diphenyl dimethyl silane; 4,4'-bis(4,4'-dimethyldibenzoyl) benzophenone; 4,4'-bis(4,4'-diethyldibenzoyl) benzophenone; 4,4'-bis(4,4'-dipropyldibenzoyl) benzophenone; 4,4'-bis(2,2'-dimethoxydibenzoyl) benzophenone; 4,4'-bis(4-dodecyldibenzoyl) benzophenone; 4,4-bis(2,2'-diacetyldibenzoyl) benzophenone; 4,4'-bis(4,4'-dimethyldibenzoyl) diphenyl methane; 4,4'-bis(4,4'-diethyidibenzoyl) diphenyl methane; 4,4'-bis(4,4'- dipropyldibenzoyl) diphenyl methane; 4,4'-bis(2,2'-dimethoxydibenzoyl) diphenyl methane; 4,4-bis(4-dodecyidibenzoyl) diphenyl methane; 4,4'-bis(2,2'-diacetyldibenzoyl) diphenyl methane; 4,4'-dibenzoyl-1,4-diphenoxy butane; 4,4'-dibenzoyl-1,2-diphenoxy ethane; 4,4'-bis(4,4'-dimethyidibenzoyl)-1,4-diphenoxy butane; 4,4'-dibenzoyl-1,12-diphenoxy-dodecane; tritoluoyl triphenyl benzene, tri(para-methoxybenzoyl) triphenyl benzene, dibenzoyl meta-terphenyl, ditoluoyl meta-terphenyl, ditoluoyl para-terphenyl, diethyldibenzoyl meta-terphenyl, dipropyldibenzoyl ortho-terphenyl, dibutyldibenzoyl para-terphenyl, dipentyldibenzoyl meta-terphenyl, dihexyldibenzoyl ortho-terphenyl, diheptyldibenzoyl para-terphenyl, dioctyldibenzoyl meta-terphenyl, dioctadecyl dibenzoyl ortho-terphenyl, and the like.

The photoinitiator is present in an amount sufficient to decrease the induction period after UV triggering. The amount of photoinitiator employed can vary broadly depending on the oxygen scavenging material employed, the wavelength, time of exposure and intensity of the radiation used, the type of photoinitiator, time of exposure and the amount of antioxidants employed, if any.

Generally, the photoinitiator will be present in an amount in the range of from about 0.001 weight percent to about 10 weight percent based on the total weight of the oxygen scavenging composition, preferably from 0.005 weight percent to 5 weight percent, and more preferably from 0.01 weight percent to 1 weight percent.

An effective photoinitiator is one which provides the oxygen scavenging composition an induction period of one day or less. The photoinitiator should be effective at 25° C. and preferably also effective at 4° C.

The photoinitiator can be introduced into the oxygen scavenging composition by any method known in the art such as coating techniques and extrusion compounding (including masterbatching). The photoinitiators can be introduced into polymers under conventional melt processing conditions to provide good mixing without plate-out on the machine.

The photoinitiator tribenzoyl triphenylbenzene can be prepared by reacting a benzoyl halide, such as benzoyl chloride, and a triphenylbenzene. The benzoyl halide and triphenylbenzene can contain additional substituents. Suitable substituents comprise any substituent which does not interfere substantially with the reaction and include alkyl, aryl, alkoxy, phenoxy, and alicylic groups containing from 1 to 24 carbon atoms or halides.

Preferably, an aluminum- or boron-containing catalyst such as aluminum trichloride or boron trifluoride is employed.

Conditions for reacting the benzoyl chloride and triphenylbenzene can vary broadly. Generally, the reaction temperature is in the range of from about −20° C. to about 150° C., preferably from about −10° C. to about 120° C. The pressure is not critical and ambient pressure is suitable. Typically, the reaction would be conducted in a suitable diluent such as nitrobenzene, chlorobenzene, dichlorobenzene, dichloromethane, dichloroethane, trichloroethane, or carbon disulfide.

The photoinitiator benzoylated styrene oligomer can be prepared by reacting styrene trimers with a benzoyl halide, such as benzoyl chloride. Styrene trimers can be distilled from a polystyrene by-products stream. The benzoyl halide and styrene trimers can contain additional substituents. Suitable substituents comprise any substituent which does not interfere substantially with the reaction and include alkyl, aryl, alkoxy, phenoxy, and alicylic groups containing from 1 to 24 carbon atoms or halides.

Preferably, an aluminum- or boron-containing catalyst such as aluminum trichloride or boron trifluoride is employed.

The reaction produces a mixture of products including the major components di-benzoylated styrene trimer, tribenzoylated styrene pentamer, tetra-benzoylated styrene pentamer, di-benzoylated styrene dimer, and minor components including benzoylated 1-phenyl naphthalene, benzoylated styrene dimer, di-benzoylated 1,3 di-phenyl propane, di-benzoylated 1-phenyl naphthalene, benzoylated 1,1-diphenyl ethane, and benzoylated ethyl-benzene.

Conditions for reacting the benzoyl halide and styrene trimers can vary broadly. Generally, the reaction temperature is in the range of from about 0° C. to about 100° C. The pressure is not critical and ambient pressure is suitable.

The photoinitiator benzoylated terphenyl can be prepared by reacting a terphenyl and a benzoyl halide, such as benzoyl chloride. The terphenyl can be para-, meta- or ortho-terphenyl. The terphenyl and benzoyl halide can contain additional substituents. Suitable substituents comprise any substituent which does not interfere substantially with the reaction and include alkyl, aryl, alkoxy, phenoxy, and alicylic groups containing from 1 to 24 carbon atoms or halides.

Generally, a catalyst such as aluminum chloride is employed. The reaction is generally conducted in a suitable solvent such as nitrobenzene, chlorobenzene, dichlorobenzene, dichloromethane, dichloroethane, trichloroethane, or carbon disulfide.

Conditions for reacting the terphenyl and benzoyl halide can vary broadly. Generally, the reaction temperature is in the range of from about 0° C. to about 100° C. The product comprising di-benzoylated terphenyl can be isolated by recrystalization from toluene.

The oxygen scavenging material can be any material known in the art to scavenge oxygen, providing that the material does not compete strongly for UV absorption in the critical region where the photoinitiator absorbs light. The oxygen scavenging material can be any organic compound or polymer which contains an oxidizable site. Preferred compounds include ethylenically unsaturated compounds and those containing benzylic, allylic and/or tertiary hydrogen. Examples of such organic compounds include squalene, dehydrated castor oil, polybutene or polypropylene.

Substituted oxidizable polymers include polymers and copolymers containing esters, carboxylic acids, aldehydes, ethers, ketones, alcohols, peroxides, and/or hydroperoxides. Preferably, the oxidizable polymers contain two or more ethylenically unsaturated sites per molecule, more preferably three or more ethylenically unsaturated sites per molecule.

Other oxidizable compounds suitable as oxygen scavenging materials include those described in U.S. Pat. Nos. 5,211,875 and 5,346,644 to Speer et al., which are hereby incorporated by reference in their entirety. Examples of oxidizable compounds include polybutadiene, polyisoprene, styrene-butadiene block copolymers, polyterpenes, poly (meta-xyleneadipamide) (also known as MXD6), polymers of fatty acids such as oleic, ricinoleic, dehydrated ricinoleic, and linoleic acids and esters of such acids, acrylates which can be prepared by transesterification of poly(ethylene-methyl acrylate) such as poly(ethylene-methyl acrylate-benzyl acrylate), poly(ethylene-methyl acrylate-tetrahydrofurfuryl acrylate), poly(ethylene-methyl acrylate-nopol acrylate) and mixtures thereof. Such transesterification processes are disclosed in U.S. Ser. No. 08/475,918 filed Jun. 7, 1995, the disclosure of which is hereby incorporated by reference. Butadiene polymers and copolymers, such as styrene-butadiene-styrene block copolymer, are preferred for low temperature applications requiring transparency.

The polyterpenes such as poly(alpha-pinene), poly(dipentene), poly(beta-pinene), and poly(limonene)are especially effective oxygen scavenger materials and produce reduced amounts of migratory carboxylic acids, aldehydes and alkenes which can produce objectionable odors and tastes.

The oxygen scavenging material can be introduced into the oxygen scavenging system by a variety of techniques. The oxygen scavenging material can be formed into films which can be a separate layer in a multi-layer structure, coated or laminated onto a material such as aluminum foil or paper, formed into bottles or other rigid containers, or even incorporated into a material such as paper, for example, in flexible and rigid packaging. The oxygen scavenging material can also be in a localized area on a layer; for example, it may be in a patch that is laminated to another layer. The oxygen scavenging composition can contain a mixture of two or more oxidizable organic compounds.

The oxygen scavenging material is generally present in the oxygen scavenging composition in an amount sufficient to scavenge at least 0.1 cc $O_2$/gram of oxygen scavenging composition/day at 25° C. Preferably, it is capable of scavenging at least about 0.5 cc $O_2$, and more preferably at least about 1 cc $O_2$/gram of oxygen scavenging composition/day at 25° C. For many applications, such as food and beverage storage, it is desirable to select an oxygen scavenging material which will effectively scavenge oxygen as indicated at a temperature of 4° C.

The amount of oxygen scavenging material employed in the oxygen scavenging composition can vary broadly depending on the desired characteristics of the final product. Generally, the oxygen scavenging material is present in an amount in the range of from about 1 weight percent to about 99 weight percent based on the total oxygen scavenging composition, preferably from about 5 weight percent to about 95 weight percent, and more preferably from 10 weight percent to 90 weight percent.

The catalyst can be any catalyst known in the art which is effective in initiating the oxygen scavenging reaction. Typical catalysts include transition metal salts. Suitable catalysts are disclosed in U.S. Pat. Nos. 5,211,875 and 5,346,644 to Speer et al., the disclosures of which were previously incorporated by reference in their entirety. Suitable transition metal salts are those which contain manganese, iron, cobalt, nickel, copper, rhodium, and ruthenium, preferably iron, nickel copper, manganese or cobalt.

Cobalt compounds containing organic or inorganic anions are preferred. Suitable anions include chloride, acetate, stearate, caprylate, palmitate, 2-ethylhexanoate, citrate, glycolate, benzoate, neodecanoate, naphthenate, oleate, and linoleate. Organic anions are preferred and cobalt oleate, cobalt linoleate, cobalt neodecanoate, cobalt stearate and cobalt caprylate are especially preferred. It has been found that a composition comprising the combination of cobalt stearate and benzoylated styrene oligomer is especially effective at scavenging oxygen at low temperature and oxygen levels, e.g., 1% oxygen levels at 4° C.

The catalyst is present in an amount sufficient to catalyze the oxygen scavenging reaction. Generally, the catalyst will be present in an amount in the range of from about 10 parts per million by weight (ppm) to about 10,000 ppm by weight transition metal ion based on the total weight of the oxygen scavenging composition, preferably from 10 ppm to 5,000 ppm transition metal ion.

The catalyst can be introduced in any manner which does not react with and/or deactivate the catalyst. For example, the catalyst can be applied onto the oxygen scavenging material by any suitable means, e.g., coating techniques such as spray coating, extrusion compounding or lamination. Further, the catalyst may be included as part of a compounded master batch using a suitable carrier resin.

The oxygen scavenging composition can be activated by methods known in the art such as by actinic radiation, i.e., ultraviolet or visible light having a wave length in the range of from about 200 nm to about 750 nm, electron beam, or thermal triggering. Such methods are described in U.S. Pat. No. 5,211,875, the disclosure of which is hereby incorporated by reference. The composition is typically activated with at least 0.1 $J/cm^2$, preferably in the range of from 0.5 $J/cm^2$ to 200 $J/cm^2$ of UV radiation in the range of from 200 nm to 400 nm, preferably in the range of from 0.5 $J/cm^2$ to 100 $J/cm^2$, and more preferably in the range of from 0.5 $J/cm^2$ to 20 $J/cm^2$. The composition can also be activated with an electron beam at a dosage of about 0.2 to 20 megarads, preferably about 1 to 10 megarads. Other sources of radiation include ionizing radiation, such as gamma, x-rays or corona discharge. The radiation is preferably conducted in the presence of oxygen.

The duration of exposure depends on several factors including the amount and type of photoinitiator present, thickness of the layers to be exposed, amount of any antioxidant present, and the wavelength and intensity of the radiation source. The activation is conducted prior to using the layer or article. Exposure to a flat layer or article provides the most uniform radiation.

For many applications, the oxygen scavenging composition can contain a diluent polymer to provide desired characteristics. Suitable diluent polymers include polyethylene, polypropylene, poly(vinyl chloride), and ethylene copolymers such as ethylene-vinyl acetate, ethylene-alkyl acrylates, ethylene-acrylic acid, ethylene-acrylic acid ionomers, and mixtures thereof.

In another aspect of the invention, the oxygen scavenging composition comprises a first phase comprising the oxygen scavenging material and a second phase comprising the catalyst. Such compositions are disclosed in U.S. Ser. No. 08/388,815 filed Feb. 15, 1995, the disclosure of which is incorporated herein by reference. The first phase is essentially devoid of catalyst. The second phase is in sufficiently close proximity to the first phase to catalyze the oxygen scavenging reaction. When the oxygen scavenging material and the catalyst are in separate phases, processing difficulties, such as deactivation of the catalyst or shortened shelf-life, are avoided.

In another aspect of the invention, the catalyst is incorporated into a polymeric material to form at least one catalyst-containing layer. This layer is then brought into contact with the oxygen scavenging material. The particular polymeric material used is not critical as long as it does not deactivate the catalyst.

In another aspect of the invention, the oxygen scavenging composition or system can include a polymeric selective barrier layer. Such compositions are disclosed in U.S. Ser. No. 08/304,303 filed Sep. 12, 1994, the disclosure of which is incorporated herein by reference. The selective barrier layer functions as a selective barrier to certain oxidation by-products, but does allow the transmission of oxygen. Preferably, the layer prevents at least half of the number and/or amount of oxidation by-products having a boiling point of at least 40° C. from passing through the polymeric selective barrier layer. Preferably, the selective barrier is located between the packaged item and the oxygen scavenging material.

The oxygen scavenging composition can also contain an oxygen barrier layer located on the outside of the scavenging layers to prevent the entry of oxygen into the sealed package. Typical oxygen barriers include poly(ethylene vinylalcohol), polyvinylalcohol, polyacrylonitrile, poly(vinyl chloride), poly(vinylidene dichloride), poly(ethylene terephthalate), silica coatings and polyamides such as Nylon 6, and Nylon 6,6 and MXD6. Copolymers of certain materials described above and metal foil layers can also be employed.

Additional layers such as adhesive layers or heat seal layers may also be employed. Adhesive layers include anhydride functionalized polyolefins.

The oxygen scavenging composition can include additives, stabilizers, plasticizers, fillers, pigments, dyestuffs, processing aids, anti-blocks, plasticizers, fire retardants, antifog agents, etc., which do not interfere with the oxygen scavenging function. The composition can also include antioxidants which inhibit the formation of free radicals and therefore improve storage of the oxygen scavenging composition prior to its use in oxygen scavenging applications. The presence of such antioxidants inhibits the initiation of the oxygen scavenging reaction until the photoinitiator is activated by radiation. Therefore, the amount employed will depend on the desired storage life of the composition, the photoinitiator, and the activation method employed.

The present oxygen scavenging compositions or systems are useful in improving the shelf-life of packaged oxygen-sensitive products such as food, pharmaceuticals, cosmetics, chemicals, electronic devices, and health and beauty products. The system can be used in rigid containers, flexible bags, or combinations of both. The system can also be used in moldings, coatings, strip/ribbon, patches, bottle cap inserts, and molded or thermoformed shapes, such as bottles and trays. In all of these applications, the oxygen scavenging composition effectively scavenges oxygen, whether it comes from the headspace of the packaging, is entrained in the food or product, or originates from outside the package.

Oxygen scavenging layers and articles are preferably prepared by melt-blending techniques. However, other methods such as the use of a solvent followed by evaporation may also be employed. When the blended composition is used to make film layers or articles, coextrusion, solvent casting, injection molding, stretch blow molding, orientation, thermoforming, extrusion coating, coating and curing, lamination, extrusion lamination or combinations thereof would typically follow the blending.

The present invention will now be described further in terms of certain examples which are solely illustrative in nature and should in no way limit the scope of the present invention.

EXAMPLES

Example 1

Tribenzoyl Triphenylbenzene

The photoinitiator tribenzoyl triphenylbenzene was prepared by placing 300 mL nitrobenzene, 152 g (1.06 mole) benzoyl chloride, and 100 g (0.33 mole) triphenylbenzene into a 2 L 4-necked flask. The mixture was warmed to about 60° C. and 348 g (2.52 moles) aluminum trichloride was slowly added over a period of about 1 hour. The temperature rose to about 80° C. and was maintained for about 4 hours. The mixture was cooled to about 40° C. The reaction mixture was poured into a solution of 340 g of HCl and 2 L water while stirring vigorously. The mixture was allowed to stand overnight and the water was decanted. The remaining mixture was filtered, washed with distilled water, and the wet cake was transferred into a 2 L 3-necked flask equipped with a mechanical stirrer. To the flask was added 900 mL distilled water. The reaction mixture was vacuum distilled until all nitrobenzene was removed. The reaction mixture was cooled, filtered and washed with water. The solid tribenzoyl triphenylbenzene was boiled in methanol, cooled and filtered. The solid was dissolved in 350 mL hot chloroform with activated carbon black and was boiled for 10 minutes and then filtered. The thus-prepared tribenzoyl triphenylbenzene solid was recrystalized again with hot chloroform, washed with methanol, and dried. The product was characterized by NMR, UV, IR and exhibited a melting point of 195° C. The molecular weight determined by mass spectrometry was 618.

Benzoylated Styrene Oligomer

A mixture of styrene trimers was distilled from a polystyrene by-products stream. Then 95 g (0.3 mol) of this trimer mixture was slowly added to a solution of 218 g (2 moles) of benzoyl chloride and 134 g (1 mole) of $AlCl_3$. After stirring overnight, the mixture was poured into a solution of 250 g NaOH in 700 ml of water and 100 g of ice with constant stirring. Then 2000 ml of toluene was added to the mixture which was stirred an additional 2 hours. The mixture was filtered to remove $Al(OH)_3$ and the organic layer was washed twice with 500 ml portions of saturated NaCl solution followed by two additional washes with 1000 ml of distilled water. The organic layer was dried overnight with $MgSO_4$. After filtering off the $MgSO_4$, the solvent was removed under vacuum on a rotary evaporator to yield 112 g of a dark brown, viscous liquid. Analysis of the product showed it comprised a mixture of mono-, di-, and tribenzoylated compounds. The mixture comprises the non-extractable photoinitiators dibenzoylated 1,1-diphenyl ethane, di-benzoylated 1,3 diphenyl propane, di-benzoylated 1-phenyl naphthalene, dibenzoylated styrene dimer, and dibenzoylated styrene trimer.

Ditoluoyl Biphenyl

The photoinitiator ditoluoyl biphenyl was prepared by placing 300 mL nitrobenzene, 38.6 g (0.25 mole) biphenyl, and then 77.3 g (0.5 mole) p-toluoyl chloride into a 1 liter 4-necked flask equipped with a water condenser. The reaction mixture was cooled to −2° C. While stirring, 66.7 g (0.5 mole) aluminum trichloride was added slowly over a period of about 20 minutes. During the reaction, the temperature increased to 14° C. The color changed from light yellow to reddish and then to dark green. The ice bath was removed and the reaction mixture was stirred at room temperature for 1 hour. The water bath temperature was increased to 67° C. and stirred for 20 hours. The temperature was increased to about 90° C. for 3 hours. The reaction mixture was poured with vigorous stirring into 1.2 L of 8% HCl solution. The mixture was stirred for ½ hour, then 2 L chloroform was added. The organic layer was separated and washed with 2×1 L sodium bicarbonate solution followed by 2×1 L water. The organic layer was dried by magnesium sulfate. The solvent was removed by vacuum and the remaining solid was washed with 2×200 mL water. The thus-produced ditoluoyl biphenyl was dissolved in 1 L chloroform and 800 mL toluene and treated with carbon black. The mixture was heated for 10 minutes and filtered hot. The thus-produced ditoluoyl biphenyl crystallized out upon cooling and was dried under vacuum overnight.

Dibenzoyl Biphenyl

The photoinitiator dibenzoyl biphenyl was prepared by placing 200 mL nitrobenzene, 38.5 g (0.25 mole) biphenyl, and 140.6 g (1.00 mole) benzoyl chloride into a 1 liter 3-necked flask equipped with a water condenser. While stirring, 160 g (1.2 mole) aluminum trichloride was added slowly over a period of about 30 minutes. During the reaction, the temperature increased from 30° C. to 55° C. The color changed from yellowish to light brown, then reddish. The flask was kept in a water bath at a temperature of 55° C. to 60° C. for 3 hours while stirring. The reaction mixture was then cooled to 35° C. The reaction mixture was poured into 1.2 L of 8% HCl solution with vigorous stirring. The organic layer was separated and poured into a blender and 500 mL n-hexane was added. The mixture was vigorously stirred for 5 minutes and then filtered. The solid was washed with n-hexane. The thus-produced dibenzoyl biphenyl was dried and recrystalized twice in chloroform.

Film Preparation

Oxidizable resin, carrier resin, catalyst and the photoinitiator to be evaluated were compounded in a twin screw extruder (Haake Rheocord TW-100 or Werner & Pfleiderer ZSK-30) at about 170° C. The carrier resin was polyethylene, PE1017, from Chevron and the oxidizable resin was styrene-butadiene-styrene copolymer, Vector 8508D from Dexco. The catalyst was 1000 ppm by weight cobalt in the form of cobalt oleate based on the total weight of the film. The indicated photoinitiator was present in the amount of 1000 ppm based on the total weight of the film. The compounded polymer containing the catalyst and 40% Vector and 60% PE1017 was pelletized. A Randcastle cast film multi-layer micro extruder was employed to create three-layer films in an "ABA" structure in which "A", the outer layers, were 0.5 mil Dowlex 3010 polyethylene and "B", the inner layer, was 1.0 mil of the compounded polymer. Total film thickness was 2.0 mils.

Head Space Oxygen Absorption

Figure 1:
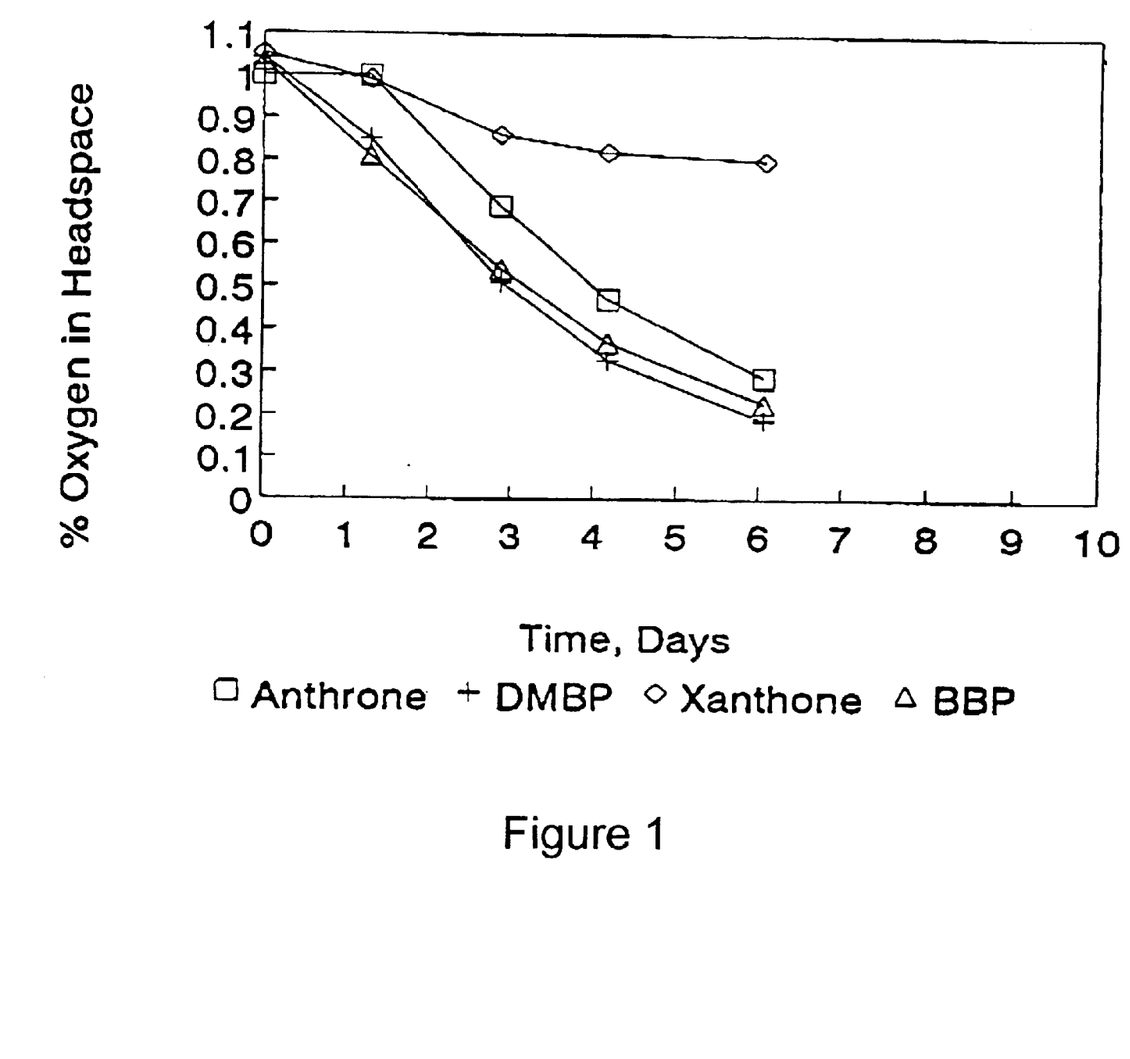
FIGS. 1, 2 and 3 are a graphic representation of the effectiveness of various photoinitiators.
Figure 2:
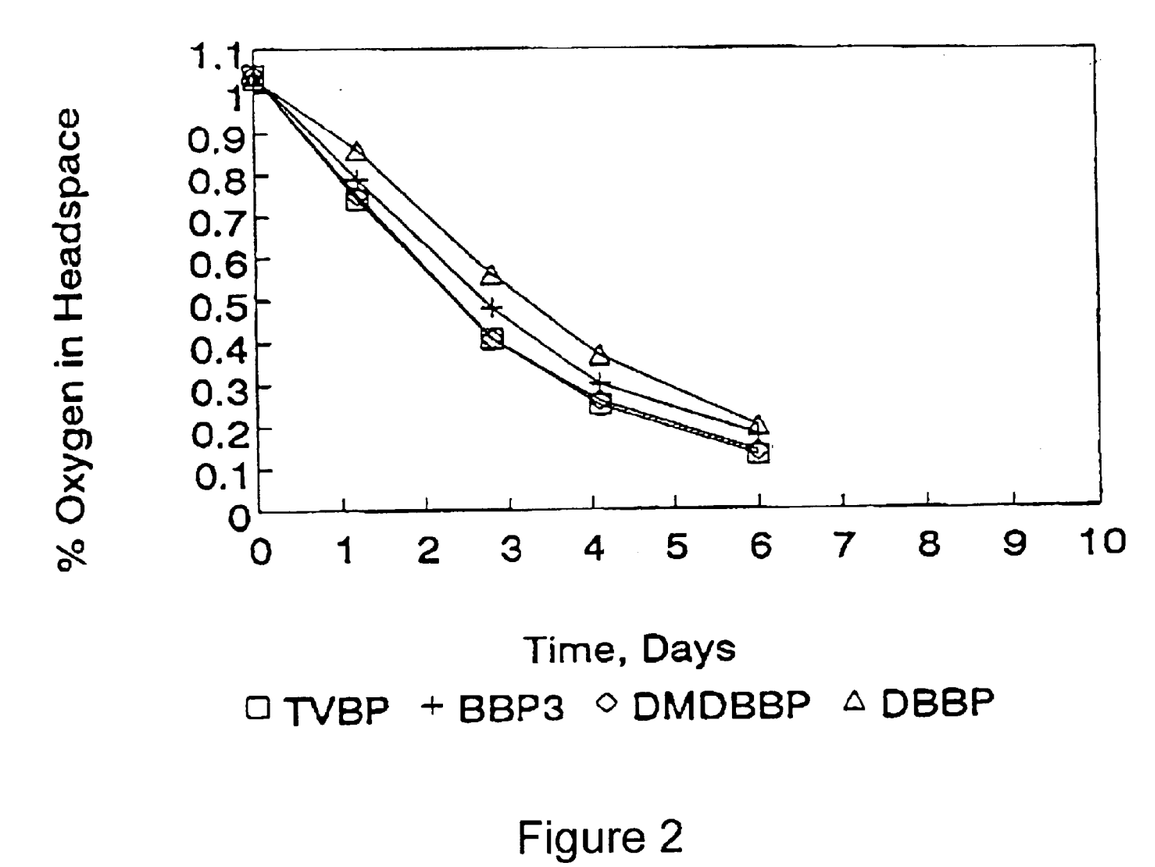

Samples of 5×20 cm size 3 layer films made above with an average weight of 0.42 gram were irradiated under a 254 nm UV lamp for a fixed period of time (e.g., 1 minute, approximately 600 mJ/cm$^2$ of light energy measured at 254 nm). The film was immediately sealed in an aluminum foil bag which was evacuated and filled with 300 mL 1% oxygen. The oxygen content was monitored by Mocon oxygen headspace analyzer for a week and oxygen level recorded. The results are graphically represented in FIGS. 1 and 2.

Extraction Test

FDA recommendations for conducting migration (extraction) studies are found in "Recommendations for Chemistry Data for Indirect Food Additive Petitions", Food & Drug Administration (Chemistry Review Branch, Office of Premarket Approval, Center for Food Safety & Applied Nutrition), Washington, D.C. 20204, Jun. 21, 1995.

Extraction tests were conducted using three methods. In the first extraction method, Method A, a 5 by 20 cm (15.5 sq. in.) piece of the film was irradiated (or not) and placed in a 20 ml headspace vial with 14 grams of ethanol. The vials were sealed with a crimped septum cap. The extraction period was 10 days at room temperature. The vials were opened and the film removed. The extracts were then stored at room temperature in the dark before testing.

In the second extraction method, Method B, a 2-inch diameter film sample was activated with 800 mJ/cm$^2$ UV, then placed in a gas tight cylindrical aluminum extraction cell. The extraction cell was flushed with gas containing 1% oxygen. A slight positive pressure was produced. Oxygen scavenging was allowed to occur within the cell at room temperature for 10 days. The oxygen scavenging results are graphically represented in FIGS. 1 and 2. Then 12.5 grams 95% ethanol was added to each cell through a septum. Residual volume of gas was set at 7–8 ml. The cell was inverted to allow contact of ethanol with the oxidized film and then placed in nitrogen cabinet at room temperature for 11 days. The extract was removed from the cells using a syringe needle in one septum and pressurizing the cell with nitrogen using a second needle in a second septum. The extracts were held in the dark at room temperature before testing.

In the third extraction method, Method C, film was extracted with Miglyol 812 (derived from coconut oil) in an extraction cell as described in Method B at a ratio of 10 g solvent/in$^2$. Samples were extracted at room temperature for 10 days.

The extracts from all methods were then analyzed for photoinitiator extractives using gas chromatography (GC-FID) or liquid chromatography (HPLC) methods which were calibrated using standard solutions of each photoinitiator. Those photoinitiators having low enough boiling points to permit them to pass through a GC column (DB-1, 0.5 mm ID, 60/5/10/300/60° C. temperature program) were analyzed using gas chromatography. Anthrone, xanthone, 4-benzoyl biphenyl and dibenzoyl biphenyl were determined by gas chromatography. The remaining compounds could not be analyzed using gas chromatography methods because of their high boiling points. Liquid chromatography methods were used for these compounds.

In Table 1 below:

ANTH is anthrone.
XAN is xanthone.
BBP is 4-benzoyl biphenyl.
BBDE is 4,4'-bis(benzoyl)-diphenyl ether.
DBBP is dibenzoyl biphenyl.
BSO is benzoylated styrene oligomer comprising benzoylated styrene dimers, trimers and pentamers.
BBP$^3$ is tribenzoyl triphenylbenzene.
DTBP is ditoluoyl biphenyl.
Good oxygen scavenging compositions consumed half of the available oxygen in less than 4 days.
Fair oxygen scavenging compositions consumed half of the available oxygen in 4–5 days.
Poor oxygen scavenging compositions consumed half of the available oxygen in greater than 6 days.
PI in extract is the amount of photoinitiator in ppb found in the extract (normalized to 10 g simulant/in$^2$ film).
DL is the detection limit defined as 3 times the instrument signal noise (normalized to 10 g simulant/in$^2$ film).

TABLE 1

| Run | Photo-initiator | Days to reach 0.5% Oxygen | Extraction Method | Triggered UV-254 | PI in Extract (ppb) | DL (ppb) |
|---|---|---|---|---|---|---|
| 101 | ANTH | NA* | A | No | 663 | 7 |
| 102 | ANTH | 4–5 | A | 1 min. | 63 | 7 |
| 103 | ANTH | 4–5 | B | 1 min. | 85 | 26 |
| 201 | XAN | NA | A | No | 870 | 6 |
| 202 | XAN | >6 | A | 1 min. | 269 | 6 |
| 203 | XAN | >6 | B | 1 min. | 218 | 29 |
| 301 | BBP | NA | A | No | 834 | 6 |
| 302 | BBP | 3 | A | 1 min. | 358 | 6 |
| 303 | BBP | 3 | B | 1 min. | 357 | 26 |
| 401 | BBDE | NA | C | 1 min. | 1125 | 50 |
| 501 | DBBP | 3–4 | A | 1 min. | 404 | 8 |
| 502 | DBBP | 3–4 | B | 1 min. | 409 | 38 |
| 601 | BSO | 2–3 | A | 1 min. | ND** | 30 |
| 602 | BSO | 2–3 | B | 1 min. | 100 | 45 |
| 701 | BBP$^3$ | 2–3 | A | 1 min. | 23 | 5 |
| 702 | BBP$^3$ | 2–3 | B | 1 min. | ND | 20 |
| 801 | DTBP | 2–3 | A | 1 min. | ND | 7 |
| 802 | DTBP | 2–3 | B | 1 min. | ND | 30 |

*Not Available
**None detected

The Table above demonstrates the low leachability of and effective photoinitiation of the inventive photoinitiators. Runs 101–401 are submitted for comparative purposes. It is believed that removal of small molecular weight compounds from the BSO photoinitiator will further reduce its leachability.

Example 2

Three layer films were prepared as described in Example 1 with the exception of employing 1000 ppm by weight cobalt in the form of cobalt stearate as catalyst and benzoylated styrene oligomer and 4-benzoyl biphenyl individually as photoinitiators. The photoinitiators were also present at 1000 ppm by weight based on the oxygen scavenging composition.

Figure 3:
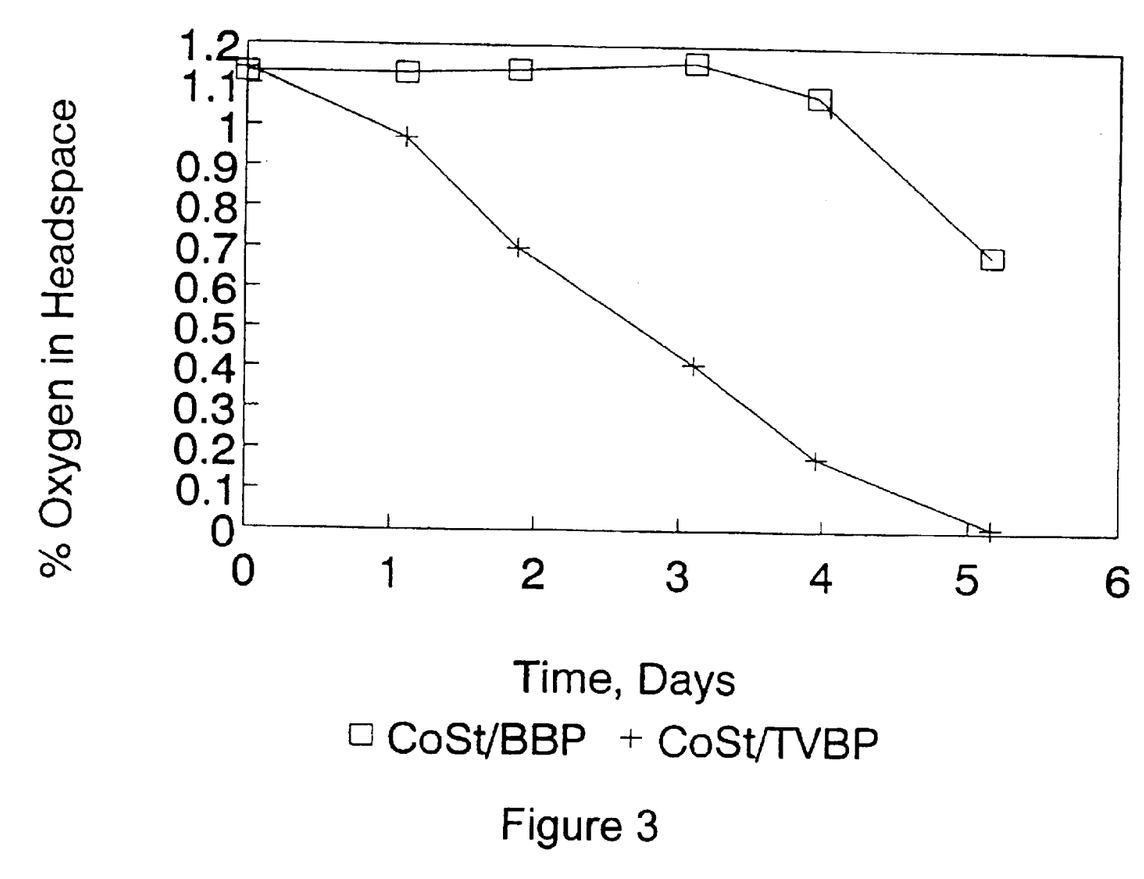

The results are graphically represented in FIG. 3. The results demonstrate the effectiveness of cobalt stearate and benzoylated styrene oligomer in providing good oxygen scavenging in a relatively short time.

Example 3

Benzoylated Meta-Terphenyl

Meta-terphenyl 115 gram (0.5 mole) and benzoyl chloride 232 grams (1.65 mole) were dissolved in 400 ml of nitrobenzene. The reactor temperature is maintained at 40–50° C. while 440 grams of aluminum chloride (3.3 mole) was added in portions to control the exothermic reaction. The reaction mixture was increased to 80° C. for 4 hours and then poured into 3 L of 5% HCl solution. The product was isolated by recrystalization from toluene and determined to be di-benzoylated meta-terphenyl. The melting point was 205–208° C. The UV spectra was similar to monomeric benzophenone. The molecular weight determined by mass spectrometer was 438 g/mole.

What is claimed is:

1. A compound, wherein the compound is a substituted tribenzoyl triphenylbenzene comprising, having one or more substituents selected from the group consisting of alkyl groups having from 1 to 24 carbon atoms, aryl groups having 1 to 24 carbon atoms, alkoxy groups having from 1 to 24 carbon atoms, phenoxy groups having from 1 to 24 carbon atoms, alicylic groups having front 1 to 24 carbon atoms, and halides.

2. A compound, wherein the compound is tribenzoyl triphenylbenzene.

* * * * *

UNITED STATES PATENT AND TRADEMARK OFFICE
CERTIFICATE OF CORRECTION

PATENT NO. : 6,852,894 B2
DATED : February 8, 2005
INVENTOR(S) : Ta Yen Ching

It is certified that error appears in the above-identified patent and that said Letters Patent is hereby corrected as shown below:

Column 6,
Line 67, after "1995," insert -- now U.S. Patent 5,627,239, --.

Column 8,
Line 43, after "1995," insert -- now U.S. Patent 5,660,761, --
Line 60, after "1994," insert -- now abandoned, --.

Column 14,
Line 26, delete "comprising".
Lines 29 and 30, delete "from".
Line 31, delete "front".

Signed and Sealed this

Seventeenth Day of May, 2005

JON W. DUDAS
*Director of the United States Patent and Trademark Office*